United States Patent [19]

Istin et al.

[11] Patent Number: 5,556,635
[45] Date of Patent: Sep. 17, 1996

[54] FILMS BASED ON COPOLYMERS, THEIR APPLICATIONS IN TRANSDERMAL SYSTEMS AND THEIR PROCESSES OF PREPARATION

[75] Inventors: Michel Istin, Gif-Sur-Yvette; Jean-Marc Grognet, Orsay; Charles Darnez, Bordeaux-Cauderan, all of France

[73] Assignee: Spi-Bio, Gif-Sur-Yvette, France

[21] Appl. No.: 284,669

[22] PCT Filed: Dec. 20, 1993

[86] PCT No.: PCT/FR93/01272

§ 371 Date: Oct. 24, 1994

§ 102(e) Date: Oct. 24, 1994

[87] PCT Pub. No.: WO94/14425

PCT Pub. Date: Jul. 7, 1994

[30] Foreign Application Priority Data

Dec. 21, 1992 [FR] France .................................. 92 15377

[51] Int. Cl.$^6$ .................................................. A61F 13/00
[52] U.S. Cl. .................................. 424/448; 424/449
[58] Field of Search .............................. 424/448, 449

[56] References Cited

FOREIGN PATENT DOCUMENTS

| 0078184 | 5/1983 | European Pat. Off. . |
| 0379045 | 7/1990 | European Pat. Off. . |
| 2250793 | 6/1975 | France . |
| 9220377 | 11/1992 | WIPO . |

*Primary Examiner*—D. Gabrielle Phelan
*Attorney, Agent, or Firm*—Oblon, Spivak, McClelland, Maier, & Neustadt, P.C.

[57] ABSTRACT

Films based on copolymers, their applications in transdermal systems and their processes of preparation. The said films consist of a hydrophobic polymer of ethylene/vinyl acetate (EVA) type containing at least one active principle and composed of 15 to 50% of hydrophilic inclusions formed from at least one hydrophilic monomer chosen from the group which comprises acrylamide, methylolacrylamide, diacetone acrylamide, maleic acid, acrylic acid, fumaric acid, itaconic acid, propylene glycol acrylate, ethylene glycol methacrylate, methacrylamide, methacrylic acid, propylene glycol methacrylate, hydroxyethyl methacrylate, dimethylaminoethyl methacrylate, N-vinylpyrrolidone, vinylacetic acid or vinylsulphonic acids.

44 Claims, 4 Drawing Sheets

FILMS BASED ON COPOLYMERS, THEIR APPLICATIONS IN TRANSDERMAL SYSTEMS AND THEIR PROCESSES OF PREPARATION

FIELD OF THE INVENTION

The present invention relates to films based on copolymers which are capable of being used as active principle matrices in transdermal systems, to transdermal systems containing the said films and to the process for the preparation of the said films and copolymers.

DISCUSSION OF THE BACKGROUND

Transdermal administration can, in certain cases, be a favourable administration route for medicaments; in fact, such a route makes it possible to optimize the systemic effect or topical effect, to increase the therapeutic effectiveness, to reduce undesirable effects and to avoid, in the case of a systemic action, the effect of a first passage through the liver.

Transdermal systems are generally forms intended to make possible the passage of active principles, incorporated in a reservoir, through the skin, either in order to have a systemic action or in order to obtain a more local action, by fixation in the underlying tissues of the skin.

Such systems can take essentially two forms:

- a bag which acts as reservoir, limited on one of its surfaces by an adhesive semi-permeable membrane placed against the skin and which controls the release and the passage of the active principle towards the skin; in this case, the membrane controls the release of the active principles and therefore, in the case of a systemic action, their blood concentration.

- a polymeric matrix which acts as reservoir and is associated with an adhesive, which controls the release towards the skin of the active principle; this form contains two variants: (1) either the polymeric matrix consists of an adhesive, with responsibility for attaching the system to the skin, which acts as reservoir, (2) or the polymeric matrix and the adhesive are separate and only the polymeric matrix acts as reservoir and controls the release of the active principle, the only function of the adhesive being to hold the system onto the skin without hindering the passage of the active principle.

The rate of release is thus controlled either by the membrane placed between the reservoir and the skin or by the reservoir itself (generally then known as matrix).

Taking into account the above, many factors must be considered in developing a transdermal system.

It is, in particular, important to have available a reservoir which makes possible a steady release of the active principle, providing a constant blood concentration or a sufficient concentration in the underlying tissues, for a sufficiently long period of time (several days), so as to avoid excessively frequent applications of such systems.

Many systems have been proposed in the prior art and recommend particularly the presence of a membrane which controls the release of the active principles and thus, in particular, their blood concentration.

In the case where the skin is not sufficiently permeable to the active principle, permeability stimulators are combined with said active principles.

Application EP 399 765, on behalf of Advanced Polymer Systems Inc., describes particularly a transdermal system including an impermeable support and a matrix, made of appropriate adhesive material such as a polyisobutylene or an acrylic, and which includes a plurality of polymeric particles; these polymeric particles include at least one penetration stimulator (or permeability stimulator), whereas the active principle to be administered can be present either in the solid form or in the liquid form in the said matrix or in the said polymeric particles.

It is specified that the choice of the matrix and of the permeability stimulator are related to the active principle; in particular, when the active principle is levonorgestrel, the matrix, which must be both a reservoir for active principles and for polymeric particles, is EVA and the stimulator is an ethyl acetate/ethanol mixture and is included in the said polymeric particles, which can be prepared from unsaturated monoethylenic monomers (acrylic or methacrylic acid esters).

International Application WO 90/07940, on behalf of Noven Pharmaceuticals Inc., describes a transdermal system which comprises an adhesive layer which includes the active principle and an impermeable support.

The adhesive layer is multipolymeric and advantageously comprises the active principle, a multipolymer containing EVA and including an acrylic polymer (adhesive), an elastomeric polymer (gum) and a tackifying agent.

The EVA copolymers (vinyl acetate: between 4 and 80 weight % and ethylene: 15 to 90%) can be either copolymers or acrylic acid/ethylene/vinyl acetate terpolymers.

The EVA/acrylate ratio is preferably between 20:1 and 1:20 by weight. A crosslinking agent can optionally be used. The composition advantageously comprises between 3 and 20% of EVA, between 25 and 70% of acrylate and between 2 and 20% of gum.

International Application WO 91/16085, on behalf of Alza Corporation, describes adhesives based on polyisobutylene (PIB) for transdermal systems.

It describes in particular a transdermal system comprising:

- a reservoir containing nicotine and comprising from 60 to 95 weight % of an EVA copolymer having a vinyl acetate content of approximately 40%,

- an adhesive layer comprising nicotine dissolved in a polymer consisting essentially of a mixture of high molecular weight PIB and of low molecular weight PIB,

- and an agent for controlling the release of the active principle, arranged between the reservoir and the adhesive.

European Patent 318,385, on behalf of Pierre Fabre Medicament, describes and claims a multilamellar device for the transdermal administration of trinitrin composed successively of a support made of a flexible and occlusive material (EVA/PVDC/EVA-type co-extruded thermoplastic film), an active adhesive reservoir based on polymers of acrylic or silicone type incorporating the active principle, a membrane for transfer of the active principle of polyurethane type, a hypoallergenic adhesive interface self-fed by the reservoir with active principle, and a protector made from a rigid or semi-rigid film coated with an anti-adhesive (ordinary paper, aluminized paper, polyesters or PVC), characterized in that it is constructed from a first module comprising the support, the active adhesive reservoir and a temporary protective paper and from a second module composed of the transfer membrane, the adhesive interface and the anti-adherent protector, the two modules being bonded to each other, after removal of the protective paper from the first module, by pressing the active reservoir against the permeable membrane for transfer of the active principle.

European Patent Application 328,806, on behalf of Paco Pharmaceutical Services, describes a transdermal system for estradiol which comprises an impermeable; support and a matrix comprising from 60 to 95% of an adhesive polymer (vinyl acetate/acrylate multipolymer), from 5 to 20% of a solvent (propylene glycol and derivatives), from 0.2 to 4% of a skin penetration stimulator (polyoxyethylene ester, polyethyleneglycolsorbitan mono-9-octadecenoic acid ester) and from 0.5% of an active principle (oestrogen and derivatives).

These documents, taken as a whole, show the variety of the transdermal devices containing particularly a polymeric matrix based on EVA; however, these devices of the prior art have a certain number of disadvantages:

the adhesive acts as reservoir, which only makes possible actions of short duration, excessively large active principle charges leading to a loss in adhesive power (limited capacity for charging with active principle);

each of the systems is only suitable for a specific active principle;

the rate of release of the active principle is related to the nature of the adhesive.

These disadvantages particularly make it difficult, with these transdermal systems, to obtain controlled blood levels of active principles, below the limiting flows due to the skin, lasting several days.

SUMMARY OF THE INVENTION

The present invention, for its part, has been devoted to the aim of supplying films capable of being used as active principle matrices in transdermal systems which correspond better to practical requirements, especially in that they can be suitable whatever the active principle, in that they make it possible to include, if necessary, significant concentrations of active principles, in that they increase the stability on storage of the active principles and particularly of unstable active principles and in that they are particularly well suited to producing controlled blood levels of active principles, below the limiting flows due to the skin, lasting several days (release of the active principle independent of the adhesive).

The present invention has also been devoted to the aim of supplying transdermal systems containing the said films and the process for the preparation of the said films.

DETAILED DESCRIPTION OF THE PREFERRED EMBODIMENTS

Figure 1:
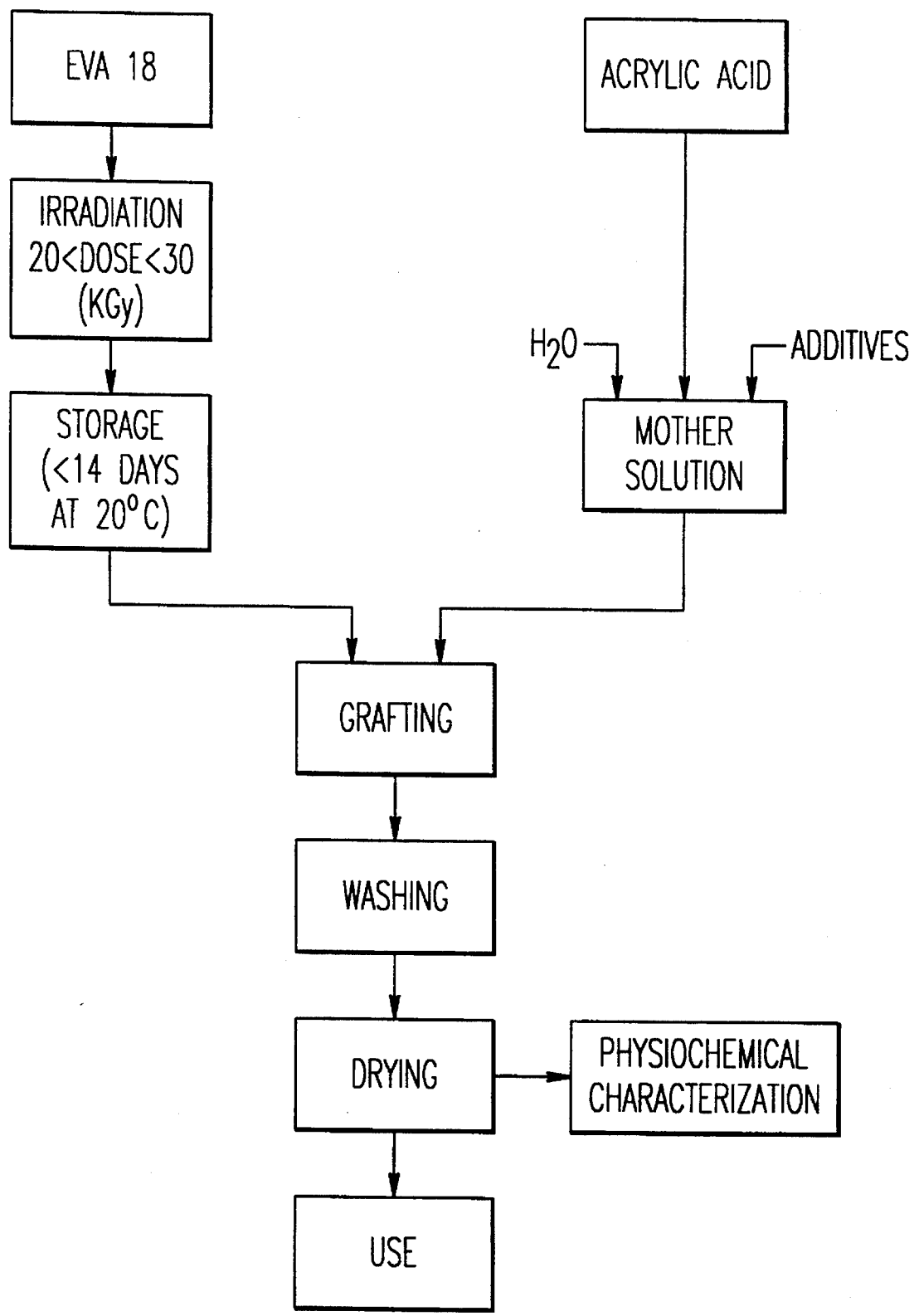
FIG. 1 represents a summary diagram of the procedure according to an indirect method of the invention.

The subject of the present invention is a film, capable of being used as active principle matrix in a transdermal system, characterized in that it consists of a hydrophobic polymer of ethylene/vinyl acetate (EVA) type containing at least one active principle and composed of 10 to 50%, preferably 15 to 50%, of hydrophilic inclusions formed from at least one hydrophilic monomer chosen from the group which comprises acrylamide, methylolacrylamide, diacetone acrylamide, maleic acid, acrylic acid, fumaric acid, itaconic acid, propylene glycol acrylate, ethylene glycol methacrylate, methacrylamide, methacrylic acid, propylene glycol methacrylate, hydroxyethyl methacrylate, dimethylaminoethyl methacrylate, N-vinylpyrrolidone, vinylacetic acid or vinylsulphonic acids.

The hydrophilic inclusions, within the meaning of the present invention, correspond to the abovementioned monomers which are polymerized, and optionally crosslinked, and grafted onto the said hydrophobic polymer (EVA). The percentage of hydrophilic inclusions depends on the monomer chosen.

According to an advantageous embodiment of the said film, the EVA comprises up to 40% of vinyl acetate, preferably 14 to 22%.

According to another advantageous embodiment of the said film, the said hydrophilic inclusions are formed from acrylic acid.

According to an advantageous arrangement of this embodiment, the percentage of acrylic acid is between 22 and 30%.

According to an advantageous mode of this arrangement, the said copolymer comprises EVA containing 14–33% of vinyl acetate, in which 22–30% of acrylic acid are grafted.

The said film preferably comprises, as copolymer, EVA containing 14–22% of vinyl acetate, in which 26% of acrylic acid are grafted; such a copolymer is hereinafter known as EVA 18/AA 26.

One of the preferred compositions by weight of the said copolymer is:

| Unit | % | parts |
| --- | --- | --- |
| Ethylene | 65.1 | 82 |
| Vinyl acetate | 14.3 | 18 |
| Acrylic acid | 20.6 | 26 |

The said film in accordance with the invention can also comprise, as copolymer, EVA containing 30–36% of vinyl acetate, in which 26% of acrylic acid are grafted; such a copolymer is hereinafter known as EVA 33/AA 26.

Unexpectedly, such copolymers and particularly the copolymer EVA 18/AA 26, as active principle matrix, provide films which simultaneously display:

mechanical properties (malleability and elasticity, particularly) which are particularly well suited to their use in a transdermal system in the form of a film, which properties are not significantly detrimentally affected by the introduction of the active principle(s) or of other charges and a charge and desorption capacity of the active principle which is also particularly well suited to a use in a transdermal system, which can even be greater than 30 weight % with respect to the copolymer and which makes it possible to envisage treatment times of the order of seven days.

In fact, the copolymers selected according to the present invention make possible the incorporation (or charging), if necessary at high concentrations, and the suitable desorption of many active principles or any other chemical substance, so as to obtain controlled blood levels of these products or active levels in the underlying tissues; such copolymers can additionally be charged with active principles in different ways (steeping, dispersion, diffusion, immersion in a saturated vapour atmosphere) and be convertible in the film form. Such copolymers also make possible an increased stabilization of the active principles which they contain.

According to another advantageous embodiment of the said film, the said hydrophilic inclusions are formed from a mixture of acrylic acid or acrylamide and N-vinylpyrrolidone.

In accordance with this embodiment, a film is obtained consisting of a terpolymer: EVA/AA/N-vinylpyrrolidone.

According to yet another advantageous embodiment of the said film, the said hydrophilic inclusions are formed from acrylamide.

The said film preferably comprises, as copolymer, EVA containing 14–22% of vinyl acetate, in which 26% of acrylamide (AAm) are grafted (EVA 18/AAm 26).

Such a copolymer has a greater hydrophilic nature than that containing acrylic acid inclusions and makes possible the incorporation of very hydrophilic active substances.

A percentage of less than 26% (of the order of 10–20%) makes it possible to obtain a copolymer with a hydrophilic nature equivalent to that of the copolymer containing acrylic acid and whose mechanical properties are particularly well suited to their use in a transdermal system.

According to another advantageous embodiment of the said film, its thickness is between 50 and 500 μm.

According to another advantageous embodiment of the said film, it comprises up to 40% of active principle.

Mention may be made, as active principle and in a non-limiting way, of NSAIs such as ketoprofen or ibuprofen, reproductive hormones such as 17β-oestradiol, optionally in combination with a progestogen, anticholinesterases, medicaments for the cardiovascular system, such as trinitrin, products used in weaning from smoking addiction, such as nicotine, medicaments for pain (morphine), antiemetics or antimigraine medicaments such as dihydroergotamine, as well as bromocriptine and substances for local use such as salicylic acid.

According to yet another embodiment of the said film, the said active principle is combined with at least one permeability stimulator, such as alcohol or polyol.

Another subject of the present invention is a transdermal system of the type comprising an occlusive support, an active principle reservoir, an adhesive interface and a protective film, characterized in that the active principle reservoir consists of a film as defined above in which the hydrophilic inclusions are formed from at least one hydrophilic monomer chosen from the group which comprises acrylamide, ethylene glycol acrylate, methylolacrylamide, diacetone acrylamide, maleic acid, acrylic acid, fumaric acid, itaconic acid, propylene glycol acrylate, ethylene glycol methacrylate, methacrylamide, methacrylic acid, propylene glycol methacrylate, hydroxyethyl methacrylate, dimethylaminoethyl methacrylate, N-vinylpyrrolidone, vinylacetic acid or vinylsulphonic acids.

Advantageously, such a transdermal system is particularly well suited to controlling the release of all kinds of active principles and has a high absorbing power of the said active principles.

Such properties are essentially linked to the characteristics of the said system, namely:

the reservoir consists of a polymeric matrix as defined above unexpectedly having the two-fold function of reservoir and of controlling the release of the active principle(s);

the rate of release of the active principles is related solely to the nature of the polymeric matrix constituting the reservoir; this means that the adhesive, combined with the said polymeric matrix, does not modify the rate of transfer of the active principle from the reservoir towards the skin;

the greater adaptability of the polymeric matrix in accordance with the invention to the active principles (one or several);

the ability of the polymeric matrix to be shaped in the form of a film of appropriate thickness;

the ability of the polymeric matrix to stabilize some of the active principles incorporated;

the high charging capacity of the polymeric matrix with active principle.

According to a preferred embodiment of the said transdermal system, it comprises:

an impermeable protective film comprising materials, used particularly in the food or pharmaceutical industry, chosen from polyvinylidene dichlorides (PVDC), polyethylenes (PE), ethylene/polyvinyl alcohol, polypropylenes, polyesters or polychlorotrifluoroethylene, an active principle matrix consisting of a film in accordance with the invention, an adhesive which is chemically inert with respect to the active principle matrix and which does not interfere in its ability to desorb the active principles, which adhesive is selected from acrylic polymers, polyurethane, silicones or EVA and a protective sheet compatible with the adhesive selected (silicone polyester, for example).

The impermeable nature of the protective film can be improved by complexing with a metal sheet, of aluminium for example, or by means of any other plating process.

According to an advantageous arrangement of this embodiment, the film in accordance with the invention, active principle matrix, is based on an EVA/AA copolymer, preferably an EVA 18/AA 26 copolymer.

According to another advantageous arrangement of this embodiment, the said film additionally comprises a stimulator of the permeability of the said active principle through the skin selected from non-toxic substances which are not a solvent of the polymeric matrix, such as alcohols and polyols (propylene gycol, PEG or ethanol, for example).

When the said transdermal system contains at least two active principles, these are either distributed in the body of the polymeric matrix or in a different segment of the polymeric matrix.

Another subject of the present invention is a process for the preparation of a film capable of being used as an active principle matrix in accordance with the invention.

The said process comprises:

(a) bringing EVA, in the powder, granule or film form, and hydrophilic monomers into contact, (b) the crosslinked polymerization of the said hydrophilic monomers and the grafting, onto the EVA, of the hydrophilic polymer obtained (EVA/hydrophilic polymer copolymerization) by irradiation until an EVA/hydrophilic polymer copolymer is obtained in which the degree of grafting of the hydrophilic polymer is between 10 and 50%, (c) the charging of the copolymeric matrix with active principle, if necessary, that is to say when the EVA is in the powder or granule form, (d) the shaping of the copolymer obtained in the form of a film.

According to an advantageous embodiment of the said process, the copolymerization stage (b) is carried out in liquid medium, in the presence of an inhibitor of homopolymerization of the hydrophilic monomers.

The said homopolymerization inhibitor is preferably a ferrous salt such as Mohr salt when, for example, acrylic acid or acrylamide is used as the hydrophilic monomer.

According to another advantageous embodiment of the said process, the copolymerization stage (b) is carried out in liquid medium in the presence of crosslinking agents chosen from the following polyunsaturated compounds: methylenebisacrylamide, divinylbenzene, triallyl cyanurate, ethylene, butylene and tetraethylene glycol acrylates or methacrylates, or triallyl orthophosphate.

This stage (b) is preferably carried out by irradiating the solution with an ionizing radiation for several hours, the total irradiation dose being between 0.5 and 50 kGy, in order to obtain the degree of grafting of the hydrophilic polymers between 10 and 50%.

The irradiation time depends on the dose rate and on the radiation source used; it is preferably between 2 hours and 30 hours.

The sources of the ionizing radiation are particularly X-ray generators, particle accelerators and in particular electron accelerators, or sources containing $^{60}Co$ and $^{137}Cs$ radioactive isotopes, which are γ-ray emitters.

According to another advantageous embodiment of the said process, the active principle charging stage (c) is carried out before the shaping stage (d).

According to another advantageous embodiment of the said process, the active principle charging stage (c) is carried out after the shaping stage (d).

The said active principle charging stage (c) can preferably be carried out:
  either by steeping,
  or by dispersion in the copolymer,
  or by diffusion from a support impregnated with active principle,
  or by immersion in a saturated vapour atmosphere.

It should, however, be noted that the method by steeping is problematic to implement industrially (safety, drying stage necessary, and the like) and leads to the use of a significant amount of active principles, much greater than the requirements of the application, and that, moreover, the method by dispersion in the copolymer is only applicable to thermostable active principles.

In contrast, the method of charging with active substance by diffusion from a support impregnated with active substance has surprisingly proved to be particularly effective and easy to apply industrially.

According to another embodiment of the said process, the shaping stage (d) is advantageously carried out by extrusion.

As a variant, the process for the preparation of the film capable of being used as active principle matrix in accordance with the invention comprises:
  (a) the irradiation of the EVA, in the powder, granule or film form, at a dose of between 10 and 80 kGy;
  (b) the storage of the irradiated EVA for several weeks at room temperature or for several months at low temperature;
  (c) the EVA/hydrophilic polymer copolymerization by bringing the irradiated EVA obtained in (b) into contact with hydrophilic monomers for several hours, preferably for 5 to 20 h, in order to obtain an EVA/hydrophilic polymer copolymer in which the degree of grafting of the hydrophilic polymer is between 10 and 50%;
  (d) the charging of the copolymer with active principle, if necessary, that is to say when the EVA is in the powder or granule form,
  (e) the shaping of the copolymer obtained in the form of a film.

The measurement of the degree of grafting on test samples must be in accordance with the invention (10–50%), after storage.

In the case where the EVA is in the film form, on conclusion of the grafting and active principle charging stages, a simple calendering will make it possible to bring the said film to the desired thickness.

Such processes of preparation make it possible:
  to obtain a great variety of polymers, which is chosen as a function of the chemical substance or active principle to be charged; and
  to remove the toxic risk related to the use of catalysts.

Another subject of the present invention is a process for the preparation of an EVA/hydrophilic inclusions copolymer as defined above, characterized in that it comprises:
  (a) the irradiation of the EVA, in the powder, granule or film form, at a dose of between 10 and 80 kGy;
  (b) the storage of the irradiated EVA for several weeks at room temperature or for several months at low temperature;
  (c) the EVA/hydrophilic polymer copolymerization by bringing the irradiated EVA obtained in (b) into contact with hydrophilic monomers for several hours in order to obtain an EVA/hydrophilic polymer copolymer in which the degree of grafting of the hydrophilic polymer is between 10 and 50%.

The EVA/monomers contact time depends on the dose absorbed, on the monomer concentration and on temperature; it is preferably between 5 and 20 hours.

According to an advantageous embodiment of the said process, the said copolymer obtained is charged with chemical substance according to one of the charging methods defined above.

Such a process makes it possible to separate the stages of the process in time, which makes possible a better adaptation to industrial application and facilitates the storage of these copolymers.

Such copolymers are particularly suited to applications in the medical, farm-produce or agronomic field which require the controlled diffusion of one or several chemical substances from a solid support which can be shaped (implant, for example, and the like).

In addition to the preceding arrangements, the invention further comprises other arrangements which will emerge from the description which will follow which refers to implementational examples of the process which is the subject of the present invention.

However, it must be well understood that these examples are given solely by way of illustration of the subject of the invention, of which they do not constitute in any way a limitation.

EXAMPLE 1

Preparation of an EVA 18/AA 26 Copolymer Capable of Being Used as a Film in a Transdermal System A. Direct Method I—Composition of the Reaction Mixture An aqueous solution containing 18.56 kg of acrylic acid is prepared in the presence of Mohr salt and then 60 kg of EVA 18, as a powder, are added to the above solution.

The main characteristics of the solution obtained are:
aqueous phase total volume ≠174.1
aqueous phase/solid phase ratio (mass): 3.0
acrylic acid/EVA ratio (mass): 0.31

II—Irradiation (Oxygen-free Atmosphere):
Dose rate: 600 Gy·h$^{-1}$
Dose absorbed: 15 kGy
Time: 24 h (reaction end determined by assaying the residual acidity)

A degree of grafting with AA of 26% is obtained over approximately 24 h.

It should be noted that these parameters can vary according to the irradiation device used.

B. Indirect Method (2-stage Method)

1) Procedure:

Polymer support:
 18%–22% EVA,

Irradiation:
 dose absorbed ≦40 kGy,
 room temperature

Storage conditions:
 room temperature (≈20° C.)

Grafting:
 reaction mixture:
  monomer: commercial grade acrylic acid
  solvent: water
  hompolymerization inhibitor: Mohr salt (c=8 g/l).
 reactor:
  glass nature
  nominal volume 1000 ml
  filling {polymer: 150 g {mother solution: $400 < V_{ml} \leq 750$
 operating conditions:
  prior deaeration: pure nitrogen flow
  temperature: 62.5°±0.5° C.

2) Results (9 experiments):

The following Tables I and II show the degree of grafting obtained by varying the following parameters: irradiation time, storage time, monomer concentration and monomer/EVA ratio by weight.

TABLE I

| Experiment No. | Dose (kGy) | Storage time (days) | AA/EVA Ratio | AA in sol. (g/l) |
|---|---|---|---|---|
| 1 | 20 | 14 | 0.4 | 150 |
| 2 | 40 | 14 | 0.4 | 120 |
| 3 | 20 | 4 | 0.4 | 120 |
| 4 | 40 | 4 | 0.4 | 150 |
| 5 | 20 | 14 | 0.6 | 150 |
| 6 | 40 | 14 | 0.6 | 120 |
| 7 | 20 | 4 | 0.6 | 120 |
| 8 | 40 | 4 | 0.6 | 150 |
| 9 | 30 | 9 | 0.5 | 135 |

TABLE II

| RESPONSES OBTAINED | | Experiment (No.) | | | | | | | | |
|---|---|---|---|---|---|---|---|---|---|---|
| | | 1 | 2 | 3 | 4 | 5 | 6 | 7 | 8 | 9 |
| Time (h) | total | 20 | 21 h 20 | 48 | 6 h 45 | 21 h 15 | 5 h 30 | 21 h 30 | 6 h 30 | 5 h 40 |
| | for τ = 15% | 10–11 | 2 h 30 | 5 | 3 | 4 h 15 | 3 | 9 | 4 | 2 h 15 |
| | for τ 28% | 20 | 12 | 50 | 5 h 45 | 12 | 5 h 10 | 18 | 7 | 5 |
| % Degree of grafting, estimated from the | acrylic a. consumption | 27.9 | 32.6 | 26.9 | 29.2 | 46.1 | 29.3 | 33.1 | 28.4 | 30.4 |
| | increase in mass | 28.9 | 32.9 | 22.3 | 29.9 | 47.4 | 30.7 | 33.3 | 27.1 | 28.4 |
| | Yd/Acrylic A. (%) | 70 | 81 | 67 | 73 | (77) | 49 | 55 | 47 | 56 |

It emerges from these experiments that the degree of grafting of 26% is reached in virtually all the experiments.

These results also show that this indirect method makes it possible to obtain:

a satisfactory agreement between the two methods of estimation of the degrees of grafting, namely by assaying the residual acrylic acid and from the variation in polymer mass before and after grafting. Moreover, these results are corroborated by the subsequent counting of the carboxyl sites attached to the material obtained, a grafting time of between 5 and 20 h (No. 3 excepted), a high yield/acrylic acid (Experiments 1, 2 and 4).

FIG. 1 represents a summary diagram of the procedure according to this indirect method.

Both the direct method and the indirect method make it possible to obtain an EVA/AA copolymer in which there is a percentage of grafted AA of the order of 26%. This copolymer can exist in the powder, granule or film form, the powder form having a particle size of up to 500 μm.

EXAMPLE 2

Preparation of a Film in Accordance with the Invention

A. From a copolymer obtained in Example 1:

1) Either the film is produced directly by hot extrusion (in the case of active principles which do not withstand heat) and the film thus obtained is then charged with active principles and excipients (including the permeability stimulator, if necessary) which are not extrusion-resistant using one of the methods mentioned above (essentially steeping or diffusion);

2) or the copolymer obtained in Example 1 is mixed, until homogeneous, with the active principle(s), the permeability stimulators and the other extrusion-resistant excipients (charging by dispersion or by immersion in a saturated atmosphere), the said mixture is then converted to granules (diameter: 2–3 mm; length: 4–5 mm) and the said granules are extruded while hot until a film is obtained in which other excipients can be added by steeping or diffusion.

B. Tests carried out on the film obtained:
 monitoring of the thickness of the film,
 tear strength (NFQ 03-011 Standard),
 tensile strength (NFT 54-102 Standard).

EXAMPLE 3

Preparation of a Film Charged with Ketoprofen and Transdermal System Obtained from this Film 1) Preparation of the EVA 18/AA 26 copolymer charged with ketoprofen:

The copolymer is obtained in accordance with Example 1.

2) Preparation of the EVA/AA, ketoprofen and propylene glycol mixture:

The film comprising ketoprofen is prepared according to Example 2, Method A.2).

The propylene glycol (PG) and EVA/AA are brought into contact for 24 hours. The ketoprofen is then added and the mixture is stirred for 30 minutes in a tilting mixer.

Granulation of the mixture:

The mixture is passed into a mixer equipped with its cutting system. The granules are stored in polyethylene bags.

Extrusion:

The EVA/AA-ketoprofen-propylene glycol granule is extruded using a die for a flat film. A tension-cooling assembly is used at the die outlet.

After extrusion, the film obtained can have a controlled thickness varying from 200 to 300 µm, according to requirements.

3) Pharmaceutical formulating: transdermal system:

The various components of the said-transdermal system are combined by known methods; a transdermal system is then obtained comprising, from the outside inwards (contact with the skin):

- a flexible aluminized impermeable film (aluminium/polyethylene complex) (support) of suitable dimensions,
- a layer of adhesive (XP 15362 B) diluted beforehand with ethyl acetate,
- the copolymer-active principle film,
- a protective film made of silicone polyester.

The system thus obtained is enclosed, for example in an envelope made from a rigid aluminized sheet (aluminium/polyethylene complex) welded onto a sheet of double-faced (silver/white) rigid aluminized film.

A. Study of desorption and of the dose of active principle charge of the film obtained.

Desorption test:

Film used:
  polymer: EVA 18/AA 26
  charge of ketoprofen: 10% of PG: 25%,
  thickness (mm): 0.30,
  surface area (cm$^2$): 7.06.

Operating conditions:
  dissolution device: Dissolutest® (USP XX) Prolabo
  desorption medium: 0.05M phosphate buffer,
  pH: 6.5,
  volume: 113 ml/cm$^2$,
  temperature: 32° C.,
  test carried out at constant volume: 800 ml.

Analytical method:
  measurement of the OD in UV spectro photometry at $\lambda_{max}$: 260 nm,
  the concentration is calculated with reference to a calibration range.

Results:

Means and standard deviations of 6 experiments (Table III).

TABLE III

| Period (hours) | Total amount desorbed (mg) | Yield of the desorption (%) | Mean degree of desorption (mg/24 h/cm$^2$) |
| --- | --- | --- | --- |
| 0 | 0.0 ± 0.0 | 0.0 ± 0.0 | |
| 0.08 | 6.6 ± 0.4 | 33.2 ± 2.0 | |
| 0.17 | 8.0 ± 0.4 | 40.1 ± 2.1 | |
| 0.25 | 8.3 ± 0.5 | 41.8 ± 2.4 | |
| 0.33 | 8.4 ± 0.5 | 42.3 ± 2.4 | |
| 0.5 | 8.7 ± 0.5 | 43.8 ± 2.6 | |

TABLE III-continued

| Period (hours) | Total amount desorbed (mg) | Yield of the desorption (%) | Mean degree of desorption (mg/24 h/cm$^2$) |
| --- | --- | --- | --- |
| 0.67 | 9.0 ± 0.5 | 45.3 ± 2.4 | |
| 1 | 9.4 ± 0.5 | 47.4 ± 2.7 | |
| 1.5 | 9.9 ± 0.6 | 49.9 ± 2.9 | |
| 2 | 10.4 ± 0.6 | 52.2 ± 2.8 | |
| 4 | 11.8 ± 0.6 | 59.3 ± 2.8 | |
| 6 | 13.1 ± 0.7 | 65.7 ± 3.6 | |
| 8 | 14.1 ± 0.9 | 71.0 ± 4.5 | |
| 24 | 18.5 ± 1.1 | 92.7 ± 5.5 | 2.61 |
| 48 | 19.9 ± 1.1 | 99.8 ± 5.5 | |

B. Monitoring of the finished product: desorption of the transdermal system based on ketoprofen.

Monitoring of the active principle charge is carried out as above in A.

Results:

Means and standard deviations of 6 experiments (Table IV).

TABLE IV

| Period (hours) | Total amount desorbed (mg) | Yield of the desorption (%) | Mean degree of desorption (mg/24 h/cm$^2$) |
| --- | --- | --- | --- |
| 0 | 0.0 ± 0.0 | 0.0 ± 0.0 | |
| 0.08 | 1.6 ± 0.5 | 7.6 ± 2.6 | |
| 0.17 | 2.1 ± 0.7 | 10.1 ± 3.4 | |
| 0.25 | 2.4 ± 0.9 | 11.8 ± 4.2 | |
| 0.33 | 2.7 ± 1.0 | 13.2 ± 4.7 | |
| 0.5 | 3.2 ± 1.1 | 15.5 ± 5.5 | |
| 0.67 | 3.6 ± 1.3 | 17.3 ± 6.2 | |
| 1 | 4.2 ± 1.5 | 20.7 ± 7.2 | |
| 1.5 | 5.0 ± 1.7 | 24.3 ± 8.5 | |
| 2 | 5.6 ± 1.9 | 27.1 ± 9.3 | |
| 4 | 7.1 ± 2.3 | 34.8 ± 11.3 | |
| 6 | 8.1 ± 2.4 | 39.6 ± 11.7 | |
| 8 | 8.9 ± 2.4 | 43.4 ± 11.9 | |
| 24 | 13.7 ± 2.6 | 66.7 ± 12.5 | 1.03 |
| 48 | 16.4 ± 1.7 | 80.2 ± 8.3 | |

EXAMPLE 4

Preparation of a Transdermal System According to the Invention (Active Principle: Trinitrin)

A preparation is carried out in a way analogous to that of Examples 1 and 2, with EVA 33 as the starting hydrophobic polymer.

An }EVA 33/AA 26 copolymer is then obtained.

A. Study of desorption and of the dose of active principle charge of the film.

desorption test:

Film used:
  polymer: EVA 33/AA 26,
  AP charge as %: 17
  thickness (mm): 0.30,
  surface area (cm$^2$): 7.06.

Operating conditions:
  Dissolution device: Dissolutest® (USP XX) Prolabo,
  desorption medium: deionized water,
  pH: 4.5–5,
  volume/unit of surface area of the film: 127 ml/cm$^2$
  temperature: 32° C.

test carried out at constant volume: 900 ml.

Analytical methods:
gas phase chromatography,
the concentration is calculated with reference to a calibration range.

Results:

TABLE V

| Period (hours) | Total amount desorbed (mg) | Yield of the desorption (%) | Mean degree of desorption (mg/24 h/cm$^2$) |
|---|---|---|---|
| 0.08 | 2.0 ± 0.4 | 5.6 ± 1.0 | |
| 0.17 | 3.0 ± 0.4 | 8.5 ± 0.9 | |
| 0.25 | 3.7 ± 0.4 | 10.7 ± 1.0 | |
| 0.33 | 4.5 ± 0.4 | 12.8 ± 1.1 | |
| 0.5 | 5.6 ± 0.8 | 16.0 ± 2.3 | |
| 0.67 | 6.7 ± 0.6 | 19.1 ± 1.8 | |
| 1 | 8.6 ± 0.4 | 24.5 ± 1.2 | |
| 1.5 | 10.6 ± 0.9 | 30.4 ± 2.1 | |
| 2 | 12.8 ± 1.1 | 36.5 ± 3.1 | |
| 4 | 20.5 ± 2.0 | 58.6 ± 5.4 | |
| 6 | 26.6 ± 2.2 | 76.2 ± 6.4 | |
| 8 | 28.1 ± 1.4 | 80.5 ± 3.7 | |
| 24 | 37.5 ± 1.3 | 107.3 ± 5.0 | 5.31 |

B. Monitoring of the finished product: desorption of a transdermal system based on trinitrin prepared in accordance with Example 2.

Monitoring of the active principle charge is carried out as above in A.

Results:

Means and standard deviations of 5 experiments

TABLE VI

| Period (hours) | Total amount desorbed (mg) | Yield of the desorption (%) | Mean degree of desorption (mg/24 h/cm$^2$) |
|---|---|---|---|
| 0 | 0.0 ± 0.0 | 0.0 ± 0.0 | |
| 0.08 | 1.0 ± 0.3 | 3.6 ± 1.2 | |
| 0.17 | 1.7 ± 0.5 | 6.5 ± 1.9 | |
| 0.25 | 2.2 ± 0.6 | 8.2 ± 2.2 | |
| 0.33 | 2.8 ± 0.9 | 10.7 ± 3.3 | |
| 0.5 | 4.7 ± 0.2 | 18.0 ± 0.9 | |
| 0.67 | 5.4 ± 0.5 | 20.5 ± 2.0 | |
| 1 | 6.7 ± 0.6 | 25.5 ± 2.2 | |
| 1.5 | 7.9 ± 0.5 | 30.0 ± 1.8 | |
| 2 | 9.1 ± 0.4 | 34.4 ± 1.4 | |
| 4 | 12.0 ± 2.0 | 45.3 ± 7.6 | |
| 6 | 14.7 ± 1.7 | 55.8 ± 6.3 | |
| 8 | 16.9 ± 1.1 | 63.9 ± 4.1 | |
| 24 | 21.3 ± 2.3 | 80.7 ± 8.6 | 3.02 |
| 48 | 25.6 ± 4.4 | 96.9 ± 16.7 | |

EXAMPLE 5

Comparison (Kinetics of the Absorption or of Desorption) of EVA 18/AA 26 and of EVA 18/AA 33: Example of Nicotine I—Absorption of nicotine by irradiated films:

A. Crosslinking of the films:
1. Nature of the films:
films obtained by extrusion of polymer powders:
a) EVA 33/AA 26
b) EVA 18/AA 26
c) EVA 33 thickness=0.3 mm and approximately 40 cm long are treated.

2. Protocol:

The films (40 cm) are placed in polyethylene sachets which are purged and filled with nitrogen before being closed by welding.

B. Absorption on films:

1. Protocol:
46 ml of an approximately 2% solution of nicotine (w/v) in water for a sample with a diameter of 24 mm and an exchange surface area equal to 9.3 cm$^2$.

A film is prepared as specified in Example 2, Method A. 1) (steeping): absorption is carried out for, on the one hand, 3 hours and, on the other hand, 24 hours at 37° C. in a shaking water bath.

At the end of absorption, the samples are wiped dry. They cannot be dried in the normal way in an oven as the nicotine is very volatile.

2. Results:

The degrees of absorption are calculated by weight uptake of the samples with reference to a control which has been subjected to the same treatment in water. They are calculated with respect to the final weight.

The results are combined in Table VII.

TABLE VII

Absorption of nicotine by different films

| Films | Wf (g) | W (mg) | Absorption (mg/g) |
|---|---|---|---|
| Absorption for 3 hours - 2% nicotine | | | |
| EVA 18/AA 26 | 0.1920 | 39 | 202 |
| EVA 33/AA 26 | 0.2132 | 37.6 | 176 |
| EVA 33 | 0.1704 | 1.4 | 8.2 |
| Absorption for 24 hours - 2% nicotine | | | |
| EVA 18/AA 26 | 0.1842 | 28.6 | 155.3 |
| EVA 33/AA 26 | 0.2591 | 79.5 | 306.8 |
| EVA 33 | 0.1709 | 2.4 | 14.0 |

Wf: weight of the film; W: weight of nicotine

II—in vitro desoration of nicotine by the films obtained in I.

A. Desorption after an absorption of three hours. 1. Protocol:
films: EVA 18/AA 26 EVA 33/AA 26: t=0.3 mm
desorption volume: 46 ml of water per sample with a diameter of 24 mm and exchange surface area of 9.3 cm$^2$. Maintenance of the temperature at 37° C. in a shaking water bath. Renewal of the medium every 2 hours.

2. Results:

They are combined in Tables VIII and IX.

TABLE VIII

Desorption of the EVA 18/AA 26 films (absorption of nicotine for 3 h)

| Time (hour) | Desorption (mg) | Desorption (cumul) | Desorption (%) | Flow (µg/h/cm$^2$) |
|---|---|---|---|---|
| 2 | 5.05 | 5.05 | 13 | 272 |
| 4 | 3.25 | 8.30 | 21 | 173.5 |
| 6 | 1.40 | 9.70 | 25 | 76.5 |
| 8 | 1.65 | 11.35 | 29 | 90 |
| 10 | 1.30 | 12.65 | 32 | 69.5 |
| 12 | 1.15 | 13.75 | 35 | 61 |

TABLE VIII-continued

Desorption of the EVA 18/AA 26 films
(absorption of nicotine for 3 h)

| Time (hour) | Desorption (mg) | (cumul) | (%) | Flow (µg/h/cm²) |
|---|---|---|---|---|
| 14 | 1.10 | 14.85 | 38 | 57.5 |

TABLE IX

Desorption of the EVA 33/AA 26 films
(absorption of nicotine for 3 h)

| Time (hour) | Desorption (mg) | (cumul) | (%) | Flow (µg/h/cm²) |
|---|---|---|---|---|
| 2 | 3.45 | 3.45 | 9 | 185 |
| 4 | 2.10 | 5.55 | 15 | 112.5 |
| 6 | 1.70 | 7.25 | 19 | 90.5 |
| 8 | 1.70 | 8.95 | 24 | 91 |
| 10 | 1.05 | 10 | 27 | 56.5 |
| 12 | 1.9 | 11.9 | 32 | 102 |
| 14 | 1.3 | 13.2 | 35 | 69.5 |

B. Desorption after absorption for 24 hours:

1. Protocol:
   Films: EVA 18/AA 26 EVA 33/AA26 EVA 33 t=0.3 mm, s=9.3cm²
   desorption volume: 46 ml of water per sample, maintenance of the temperature at 37° C. in a shaking water bath.
   Renewal of the medium every 2 hours.
2. Results:
   They are combined in Tables X, XI and XII.

TABLE X

Desorption of nicotine from EVA 33 films
(absorption for 24 h)

| Time (hour) | Desorption (mg) | (cumul) | (%) | Flow (µg/h/cm²) |
|---|---|---|---|---|
| 2 | 1.25 | 1.25 | 52 | 67 |
| 4 | 0.10 | 1.35 | 56 | 4.5 |
| 6 | 0.02 | 1.37 | 57 | 1 |
| 8 | 0.01 | 1.38 | 57.5 | 0.5 |
| 10 | 0.01 | 1.39 | 58 | 0.5 |
| 12 | 0.01 | 1.40 | 58 | 0.5 |
| 14 | 0.01 | 1.41 | 59 | 0.5 |

TABLE XI

Desorption of nicotine from EVA 18/AA 26 films
(absorption for 24 h)

| Time (hour) | Desorption (mg) | (cumul) | (%) | Flow (µg/h/cm²) |
|---|---|---|---|---|
| 2 | 7.1 | 7.1 | 25 | 383.5 |
| 4 | 3.4 | 10.5 | 37 | 182 |
| 6 | 2.5 | 13 | 46 | 135 |
| 8 | 1.2 | 14.2 | 50 | 68 |
| 10 | 1 | 15.2 | 53 | 54 |
| 12 | 0.8 | 16 | 56 | 43 |
| 14 | 0.7 | 16.7 | 59 | 37 |

TABLE XII

Desorption of the EVA 33/AA 26 films
(absorption for 24 h)

| Time (hour) | Desorption (mg) | (cumul) | (%) | Flow (µg/h/cm²) |
|---|---|---|---|---|
| 2 | 19.6 | 19.6 | 25 | 1055 |
| 4 | 6 | 25.6 | 32 | 325 |
| 6 | 4.1 | 29.7 | 37 | 250 |
| 8 | 2.5 | 32.2 | 40 | 135 |
| 10 | 1.9 | 34.1 | 43 | 103 |
| 12 | 1.8 | 35.9 | 45 | 95 |
| 14 | 1.7 | 37.6 | 47 | 90 |

These data particularly show that EVA 18/AA 26:

makes it possible to rapidly reach the maximum absorption charge (see Table VII);

has a rapid desorption rate.

EXAMPLE 6

Comparison of the Behaviour of EVA 18/AA 26 and of EVA 18/AA 16: Example of Nicotine

TABLE XIII

Synoptic table of the main results emerging from the physicochemical analysis of the supports.

| Comparision criterion | | Copolymer type | |
|---|---|---|---|
| | | EVA 18/AA 16 | EVA 18/AA 26 |
| Percentage | C | 68.7 ± 0.1 | 71.5 ± 0.3 |
| composition | H | 10.9 ± 0.1 | 11.4 ± 0.1 |
| (%) | O | 18.2 ± 0.1 | 17.0 ± 0.1 |
| | N | inf. at 1% | inf. at 1% |
| Exchange capacity | (mEq · g⁻¹) | 1.91 ± 0.11 | 2.87 ± 0.04 |
| Estimated degree of grafting | (%) | 15.9 ± 0.9 | 26.0 ± 0.4 |
| Mass loss (%) by thermogravimetric analysis | 150° C. | 1.3 | 0.6 |
| | 250° C. | 3.3 | 1.9 |
| | 400° C. | 25.3 | 22.1 |
| | 500° C. | 91.7 | 90.8 |
| Infrared spectrometry | CH₂ | + | + |
| | C=O ester | + | + |
| | C—O—C | + | + |
| | C=O acid | + | + |
| | OH acid | + | + |
| Mass spectrometry (m/e) | 72 | + | + |
| | 86 | + | + |
| | 99 | + | + |
| | 13 | + | + |
| Water-soluble fraction | (%) | 4.2 | 2.8 |
| Toluene-soluble fraction | (%) | 62 | 51 |

TABLE XIV

Synoptic table of the main results emerging from the behavioural study of the supports.

| Comparison criterion | | Copolymer type | |
|---|---|---|---|
| | | EVA 18/AA 16 | EVA 18/AA 26 |
| Charging time of the powders | (min) | 15 | 15 |

TABLE XIV-continued

Synoptic table of the main results emerging from the behavioural study of the supports.

| | | Copolymer type | |
|---|---|---|---|
| Comparison criterion | | EVA 18/AA 16 | EVA 18/AA 26 |
| Degree of charging of the powders | (%) | 35 | 25 |
| Amount of water after charging | (%) | 379 | 148 |
| Desorption kinetics of the powders | (mg/45 min) | 78 | 74 |
| Degree of charging of the films | (mg · cm$^{-2}$) | 7.78 ± 0.56 | 6.40 ± 0.30 |
| Increase in the surface area after impregnation | | 2.6 | 1.9 |
| Increase in the surface area after drying | | 1.4 | 1.3 |
| Increase in weight after impregnation | | 4.7 | 2.9 |
| Increase in weight after drying | | 2.0 | 1.8 |
| Amount of water after charging | (mg · cm$^{-2}$) | 24.1 | 17.1 |
| Amount of water after drying | (mg · cm$^{-2}$) | 6.6 | 7.7 |
| Desorption kinetics of the films | | | |
| Half-life of the first phase | (hour) | 0.63 | 0.81 |
| Half-life of the last phase | (hour) | 20.1 | 20.1 |

These data also show the advantage of the EVA 18/AA 26 copolymer. The amount of water absorbed during the charging is very markedly increased in the case of the use of EVA 18/AA 26; this leads to a significant swelling of the film and detrimentally affects its mechanical properties.

EXAMPLE 7

Preparation of a Film Charged with Physostigmine and Transdermal System Obtained from this Film 1) Preparation of the EVA 18/AA 26 copolymer charged with physostigmine at 5 mg/cm$^2$:

The copolymer is obtained in accordance with Example 1.

2) Preparation of the EVA/AA and physostigmine mixture:

The film comprising the physostigmine is prepared according to Example 2, Method A. 1):

The incorporation of the physostigmine is carried out by impregnating the film in an ethanolic solution of physostigmine.

The charging conditions are the following:

composition of the H$_2$O/EtOH solution: 80/20 (v/v);

concentration of the solution with physostigmine: 20 mg/ml;

steeping conditions; sheltered from the light and with stirring for 3 hours.

Such a charging time makes it possible to obtain a degree of charge of around 5 mg/cm$^2$.

3) Pharmaceutical formulating: transdermal system:

The various components of the said transdermal system are combined by known methods; a transdermal system is then obtained comprising, from the outside inwards (contact with the skin), the same constituents as in Example 3.

A. Study of the desorption and of the dose of active principle charge of the film obtained.

Figure 2:
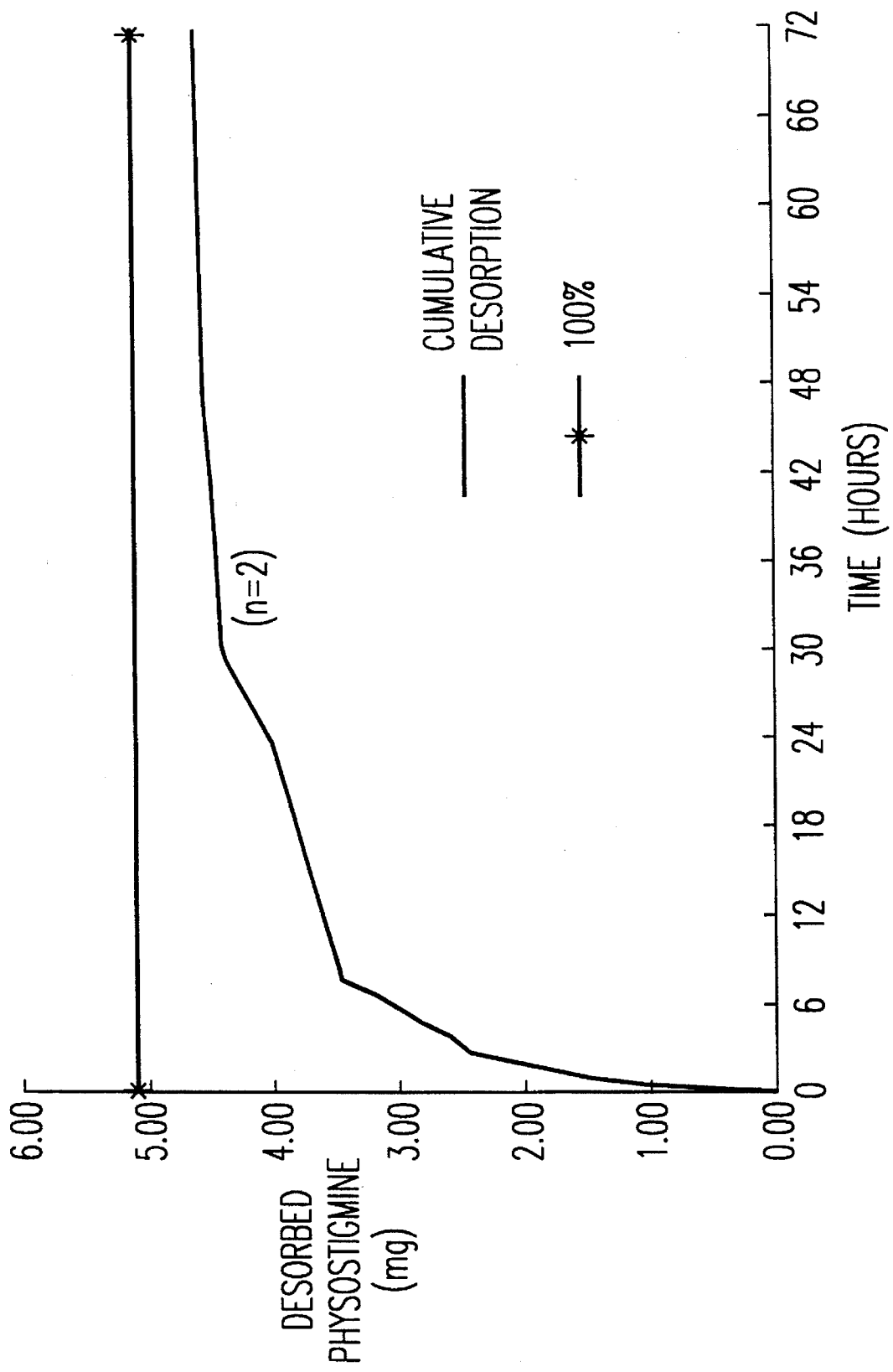
FIG. 2 shows desorption curves used in water at 37° C. on film disks of Example 7.

Desorption test:

Desorption curves were produced, in water at 37° C., on film disks charged under the preceding conditions, 3 days and 38 days after charging. These curves are represented in FIG. 2 (abscissa: time (hours), ordinate: physostigmine charged (mg/cm$^2$)).

A progressive desorption of the physostigmine released by the film is observed.

50% of what had been fixed is desorbed over 3 hours (T50) and more than 90% after 72 hours (T90). The non-releasable fraction is low (less than 10%). The two curves are virtually identical, showing a stability of the desorption conditions during the time spent (38 d).

B. Monitoring of the finished product: desorption of the transdermal system based on physostigmine.

Monitoring of the charge is carried out by HPLC assay, preceded by an extraction of the physostigmine from the film.

The stability of the degree of charge was verified over six weeks. Variation in the degree of charge with time was not revealed, this degree being constant at around 5 mg/cm$^2$.

C. Pharmacokinetic study of the release of the active principle from the said transdermal system.

Pharmacokinetic and pharmacological studies carried out in rabbits during the application of transdermal systems with diameters of 50, 20 and 12 mm (19.63, 3.14 and 1.13 cm$^2$ surface area) showed that the plasma physostigmine concentrations are maintained at a plateau throughout the application time and its activity by modification of the cholinesterase activity.

The transdermal system delivers the physostigmine with an effective mean flow of 6.29±2.6 μg/h·cm$^2$.

The half-life of the physostigmine after removal of the patch is equivalent to the half-life after intravenous physostigmine administration and assay of the physostigmine in the skin reveals negligible physostigmine levels. There thus exists no reservoir phenomenon in the skin.

EXAMPLE 8

Preparation of a Film Charged with 17β-oestradiol and Transdermal System Obtained from this Film 1) Preparation of the EVA 18/AA 26 copolymer charged with 7% 17β-oestradiol:

The copolymer is obtained in accordance with Example 1.

2) Preparation of the EVA/AA, 17β-oestradiol, propylene glycol and polyethylene glycol 400 mixture:

The film comprising 17β-oestradiol is prepared according to Example 2, Method A.2):

The propylene glycol, the PEG 400 and the EVA/AA are brought into contact for 24 hours, the 17β-oestradiol is then added and the mixture is stirred for 30 min in a tilting mixer.

The preparation is then carried out as in Example 3.

When the film is produced, it is charged with ethanol either by immersion in a saturated ethanol atmosphere (Example 2, Method A.2) or by diffusion from a support impregnated with ethanol (Example 2, Method A.1) in order to increase the cutaneous passage of the estradiol.

3) Pharmaceutical formulating: transdermal system:

The various components of the said transdermal system are combined by known methods; a transdermal system is then obtained comprising, from the outside inwards (contact with the skin):

- a flexible aluminized impermeable film (aluminium/polyethylene complex) (support) of suitable dimensions: 40 cm$^2$,
- a layer of adhesive (XP 15362 B: acrylic copolymer) diluted beforehand with ethyl acetate: 80 mg,
- the copolymer-active principle film: 1200 mg, with 60 mg PEG 400 and 300 mg PG,
- a protective film made of fluorinated polyester: 40 cm$^2$.

The system thus obtained is enclosed, for example in an envelope made from a rigid aluminized sheet (aluminium/polyethylene complex) welded onto a sheet of double-faced (silver/white) rigid aluminized film.

The various components of the transdermal system are subjected to the same in vitro monitorings as previously (see Example 3).

Pharmacokinetic studies carried out on post-menopausal women during the application of 40 cm$^2$ transdermal systems showed that the 17β-oestradiol blood concentrations remain, for at least 4 days, the same as concentrations accepted as being effective. The mean concentration is 34±7 pg/ml between 0 and 96 hours, as the following results show:

Samples taken before exposure of the transdermal system in accordance with the invention (t=−24 h) give the base level of 17β-oestradiol, which is of the order of 6±1 pg/ml.

Table XV below shows the mean values of the plasma concentrations from the transcutaneous passage of estradiol after application of a transdermal system in accordance with the invention for 96 h (n=4).

TABLE XV

| Time (hours) | Plasma concentrations | | |
|---|---|---|---|
| | means | ± | standard deviation |
| −24 | 6 | ± | 1 |
| 0 | 15 | ± | 12 |
| 5 | 55 | ± | 16 |
| 9 | 68 | ± | 28 |
| 24 | 47 | ± | 10 |
| 29 | 34 | ± | 12 |
| 33 | 35 | ± | 18 |
| 48 | 29 | ± | 17 |
| 72 | 28 | ± | 16 |
| 96 | 25 | ± | 8 |
| 120 | 8 | ± | 2 |

EXAMPLE 9

Charging a Matrix with Ethanol by Diffusion from a Support (Nonwoven) Impregnated with Active Principle (17β-oestradiol).

TABLE XVI

| Transfer time | Mean alcohol content (n = 2) | |
|---|---|---|
| | (mg) | (%) |
| 1.5 | 6.9 | 21 |
| 4 | 8.8 | 28 |
| 6 | 9.1 | 27 |
| 24 | 9.0 | 27 |
| 48 | 9.7 | 29 |

This Table XVI shows the results of charging a film charged with 17β-oestradiol in accordance with Example 8 with ethanol by diffusion from a nonwoven support impregnated with ethanol.

This illustrates that, from 1 h 30, degrees of charging with ethanol are obtained which are sufficient for transdermal application.

Figure 3:
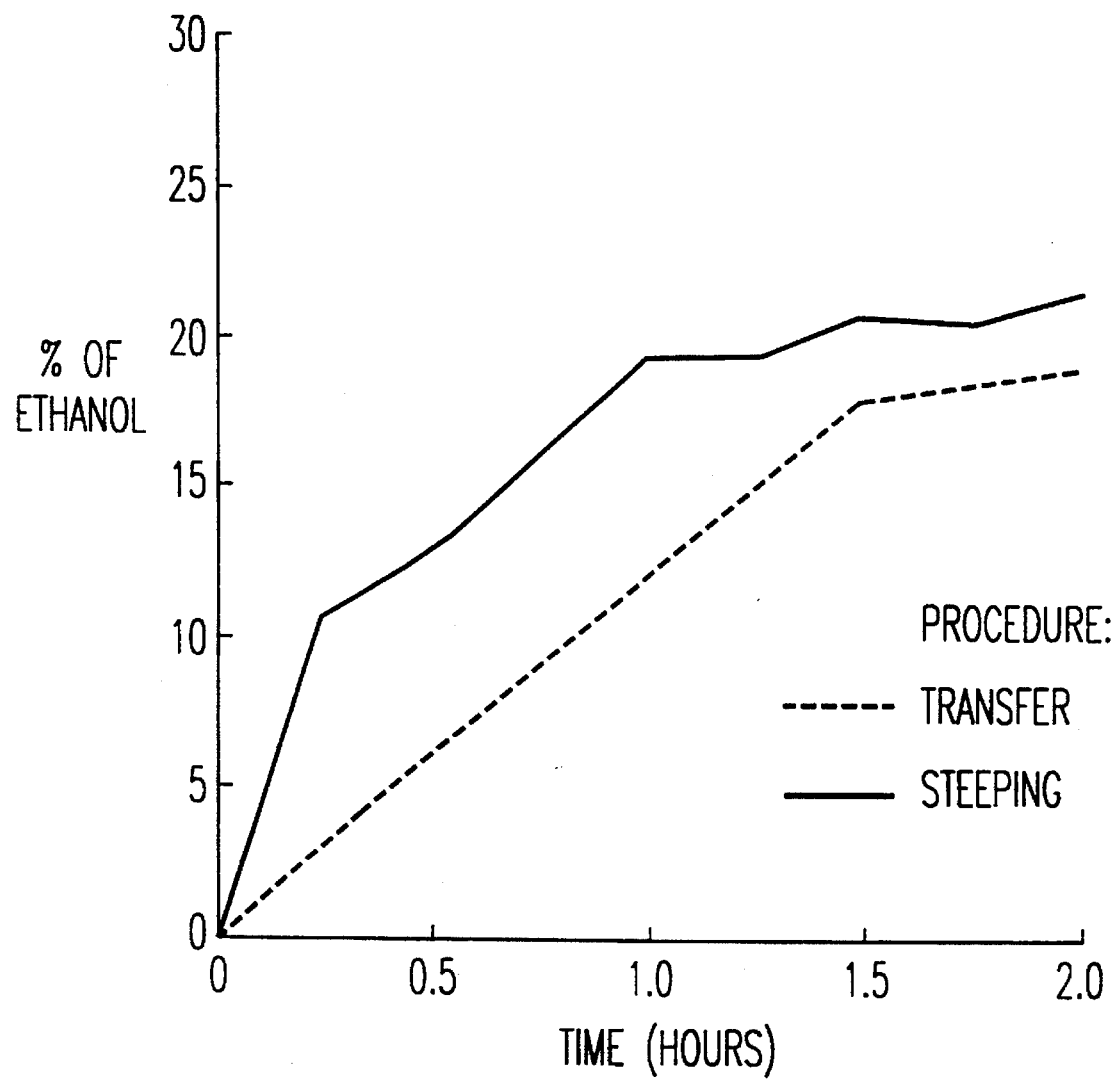
FIG. 3 compares the results of charging a matrix with ethanol by diffusion and by steeping (see Example 9).

FIG. 3 compares this new method of charging (diffusion) with charging by steeping, the disadvantages of which were recalled above, and shows the equivalence of these charging processes.

EXAMPLE 10

Preparation of an EVA/AAm Copolymer Capable of Being Used as Film in a Transdermal System 1) Procedure:

The preparation of the solutions, the degassing, the grafting, the washings and the drying are carried out as specified in Example 1, with acrylamide as the hydrophilic monomer.

In particular, irradiation of EVA 20 (Exxon) is carried out at a dose of between 20 and 40 kGy and is followed by an ageing at room temperature of between 4 and 10 days; the acrylamide (AAm)/EVA ratio by mass is between 0.4 and 0.6 and the concentration of acrylamide in aqueous solution of the order of 150 g.l$^{-1}$.

More precisely, the procedure comprises:

a) irradiation of the sample with a dose of 40 kGy under a 17 MeV electron beam, resulting from a linear accelerator and characterized by a dose rate of the order of 1.5×10$^6$ Gy.h$^{-1}$, according to the operating conditions adopted, b) heating while sheltered from the air for 7 h at 60° C. in a 20% acrylamide solution in water containing 4 g.l$^{-1}$ of Mohr salt.

After washing and drying, a degree of grafting equal to 25% is found by gravimetry, the grafting kinetics being monitored by refractometry or UV spectrophotometry on samples withdrawn at intervals from the grafting solution.

2) Results (4 tests):

Table XVII shows the degree of grafting obtained by varying the following parameters: irradiation time, storage time (ageing), monomer concentration and monomer/EVA ratio by weight.

TABLE XVII

| Test No. | Dose absorbed (kGy) | Ageing time (days) | AAm/ EVA | Reaction time (min) | Time τ = 15% (min) | Time τ = 28% (min) | τ estimated by UV (%) | τ by weight (%) |
|---|---|---|---|---|---|---|---|---|
| 1 | 30 | 9 | 0.5 | 360 | 230 | 375 | 27.3 | 33.0 |
| 2 | 40 | 7 | 0.6 | 285 | 100 | 290 | 27.8 | 26.8 |
| 3 | 20 | 4 | 0.6 | 375 | — | — |  | 18.3 |
| 4 | 40 | 7 | 0.4 | 375 | 290 | 530 | 19.5 | 21.6 |

It emerges from these tests that the degree of grafting of 26% is achieved in virtually all the experiments; it is observed that there is reasonable equivalence between the values of the degree of grafting estimated by UV spectrophotometry and by weight.

These results also show that:

the rate of grafting becomes faster as the dose absorbed becomes greater (Tests 2 and 3), the amount of acrylamide with respect to EVA is high (Tests 2 and 4), AAm Test No. 1 shows kinetic parameters similar to those of Test No. 9 of grafting with acrylic acid, carried out under the same conditions, the best results obtained with acrylamide (AAm Test No. 2) are also comparable to those obtained with acrylic acid (Test No. 4).

3) Characterization of the copolymers obtained:

As in the case of acrylic acid, the EVAs grafted with acrylamide were characterized by different techniques in order, on the one hand, to verify their structure (nature of the grafts, degree of grafting, and the like) and especially to verify that they possessed the hoped-for hydrophilic properties.

a) Elemental analysis:

This technique, not suited to EVAs grafted with acrylic acid, is again of interest on account of the introduction of a heteroatom, in this case nitrogen. The content of this element, which is not present in the starting EVA, is capable of varying sufficiently significantly to be able to be correlated, without too much error, with the degree of grafting with acrylamide.

Thus, if the respective fractions by weight of ethylene, vinyl acetate and acrylamide in the grafted polymer are known as x, y and z (on the basis of x+y =100% and z=τ), there is obtained:

$$\%N = \frac{19.774z}{(x+y+z)} \text{ or } \tau = \frac{100 \cdot \%N}{19.774 - \%N}$$

Comparison of the different values of the degree of grafting (estimated values, values by weight and values recalculated from the nitrogen content) discloses great similarity. On the one hand, for the same sample, with one exception, the nitrogen content varies little from one sampling to another, which testifies to homogeneous grafting. On the other hand, the recalculated degrees of grafting agree very well with the other values and thus confirm the validity of the kinetic monitoring by UV.

TABLE XVIII

| Test No. | % C | % H | % N | Degree of grafting (%) recalculated from % N | by weight |
|---|---|---|---|---|---|
| 1 | 70.14 | 11.66 | 5.02 | 34.0 | |
|  | 70.25 | 11.90 | 4.40 | 28.6 | 30.6 ± 2.4 | 33.0 |
|  | 69.63 | 11.27 | 4.47 | 29.2 | | |
| 2 | 71.32 | 11.59 | 3.89 | 24.5 | | |
|  | 72.46 | 11.75 | 3.71 | 23.1 | 24.6 ± 1.3 | 26.8 |
|  | 70.76 | 11.20 | 4.12 | 26.3 | | |
| 3 | 74.18 | 11.64 | 2.95 | 17.5 | | |
|  | 73.59 | 11.64 | 3.01 | 18.0 | 17.7 ± 0.2 | 18.3 |
|  | 73.69 | 11.42 | 2.96 | 17.6 | | |
| 4 | 73.44 | 11.18 | 3.43 | 21.0 | | |
|  | 72.79 | 11.36 | 3.56 | 22.0 | 21.5 ± 0.5 | 21.6 |
|  | 72.26 | 11.22 | (6.57) | (49.8) | | | b) Moisture uptake:

The hydrophilicity of the grafted polymers was evaluated from their moisture uptake Wm (expressed in ‰ by mass). This characteristic of each material is related to its structure by an additivity relationship which, in the case of the grafting of acrylamide, is expressed according to the relationship (1):

$$Wm (\permil) = \frac{18,000}{100+\tau} \left[ \frac{VA}{86} \cdot Hi\,(ester) + \frac{\tau}{71} \cdot Hi\,(amide) \right]$$

where the Hi values represent the elementary contributions of the hydrophilic links. The latter are a function of the relative humidity and are calculated by interpolation of the Van Krevelen values:

TABLE XIX

| Relative humidity RH (%) | 44 | 65 | 81 | 97 |
|---|---|---|---|---|
| Hi(CO$_2$CH$_3$) | 0.04 | 0.07 | 0.11 | 0.19 |
| Hi(CONH$_2$) | 0.45 | 0.69 | 1.16 | 1.85 |

The following Table shows a synthesis of the experimental results (first value) and of the values recalculated from the relationship (1) with the degree of grafting by weight (first parenthesis) or the degree from the nitrogen content (second parenthesis):

TABLE XX

| Test No. | Degree of grafting (%) by weight | Degree of grafting (%) % N | Moisture uptake at equilibrium, Wm (%) RH = 44% | Moisture uptake at equilibrium, Wm (%) RH = 65% | Moisture uptake at equilibrium, Wm (%) RH = 81% | Moisture uptake at equilibrium, Wm (%) RH = 97% |
|---|---|---|---|---|---|---|
| 1 | 33.0 | 30.6 | 23(30)(28) | 42(46)(43) | 62(76)(72) | 174(122)(116) |
| 2 | 26.8 | 24.6 | 16(26)(24) | 30(39)(37) | 51(66)(62) | 121(105)(99) |
| 4 | 21.5 | 21.5 | 15(22)(22) | 26(33)(33) | 46(56)(56) | 123(90)(90) |

As in Example 1 (EVA grafted with acrylic acid), the moisture uptake increases with the relative humidity (RE) and, for a given relative humidity, with the degree of grafting.

If these experimental values are compared with those obtained above for acrylic acid, it is noticed that, for a comparable degree of grafting (of the order of 25 to 30%), the moisture uptake of the EVAs grafted with acrylamide is approximately 10 to 20% greater than that of their acid homologues.

Figure 4:
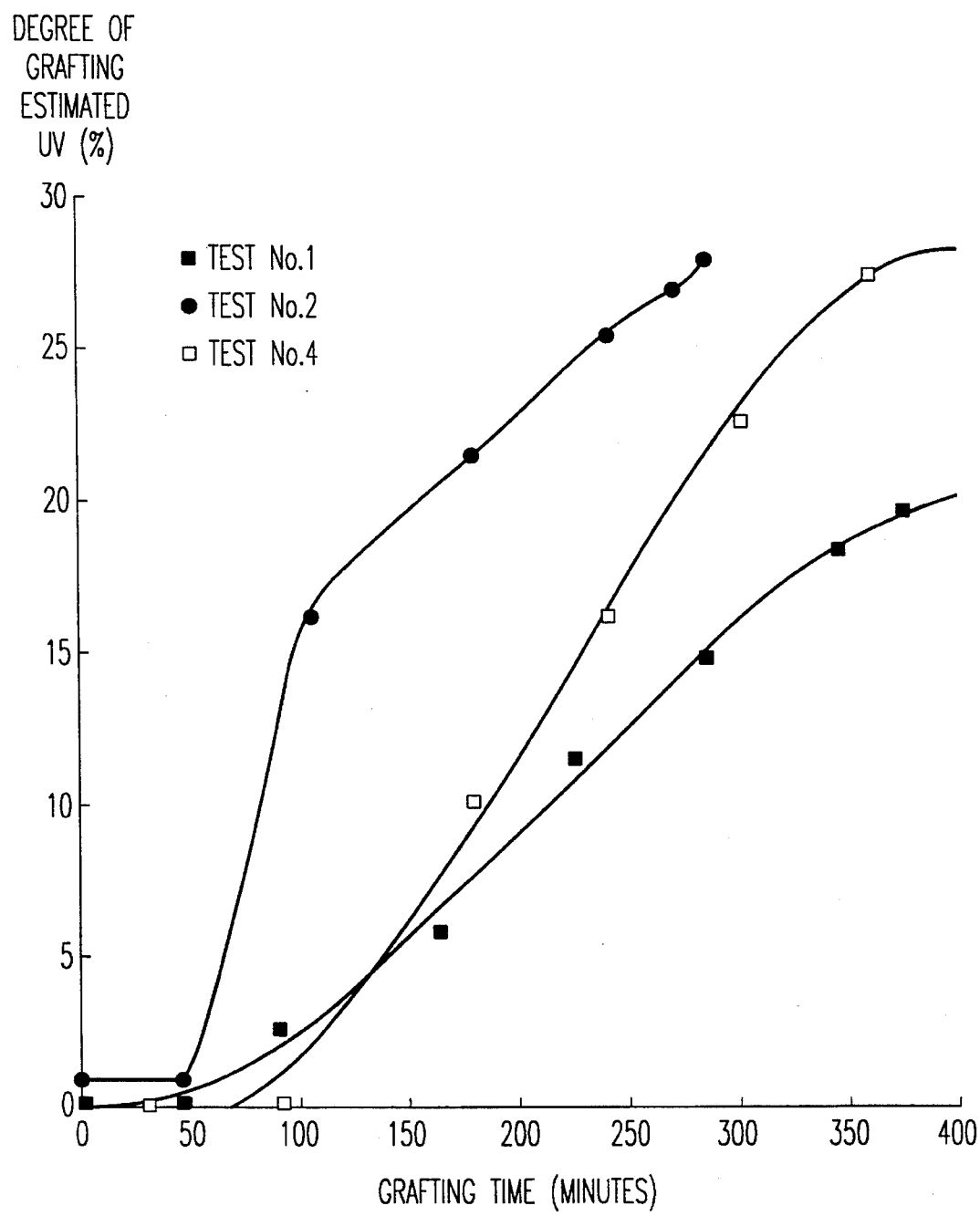
FIG. 4 illustrates the degree of grafting obtained as a function of grafting time for Example 10.

FIG. 4 illustrates the degree of grafting obtained (estimated by UV in %) as a function of the grafting time (minutes).

Grafted copolymers are obtained which are more hydrophilic than those obtained with acrylic acid.

EXAMPLE 11

Preparation of an EVA/acrylic Acid Copolymer Capable of Being Used as Film in a Transdermal System The EVA is directly used in the film form (film with a thickness of 70 μm).

The procedure comprises:

a) irradiation of the sample (dose rate $=5$ kGy.h$^{-1}$, dose absorbed: 30 kGy) Cobalt-60 source b) heating for 8 hours at 60° C. in an oxygen-free medium in a 25% aqueous acrylic acid solution containing 20 g.l$^{-1}$ of Mohr salt.

In addition to that which emerges from the above, the invention is in no way restricted to those of its implementations, embodiments and application modes which have just been described more explicitly; on the contrary, it embraces all the variants thereof which can come to the mind of a technologist in the subject, without departing from the context or from the scope of the present invention.

We claim:

1. A film, capable of being used as an active principle matrix in a transdermal system, comprising:

a hydrophobic ethylene/vinyl acetate polymer containing at least one active principle and composed of 10–50 wt. % of hydrophilic inclusions consisting of a hydrophilic polymer formed from at least one hydrophilic monomer selected from the group consisting of acrylamide, methylolacrylamide, diacetone acrylamide, maleic acid, acrylic acid, fumaric acid, itaconic acid, propylene glycol acrylate, ethylene glycol methacrylate, methacrylamide, methacrylic acid, propylene glycol methacrylate, hydroxyethyl methacrylate, dimethylaminoethyl methacrylate, N-vinylpyrrolidone, vinylacetic acid and vinylsulfonic acids.

2. The film of claim 1, wherein said ethylene/vinyl acetate polymer comprises up to 40 wt. % vinyl acetate.

3. The film of claim 2, wherein said ethylene/vinyl acetate polymer comprises 14–22 wt. % vinyl acetate.

4. The film of claim 1, wherein said hydrophilic monomer comprises acrylic acid.

5. The film of claim 4, wherein said ethylene/vinyl acetate polymer comprises 22–33 wt. % acrylic acid.

6. The film of claim 5, wherein said ethylene/vinyl acetate polymer is an ethylene/vinyl acetate graft copolymer comprising 14–33 wt. % vinyl acetate and having 22–30 wt. % acrylic acid grafted thereto.

7. The film of claim 6, wherein said graft copolymer comprises 14–22 wt. % vinyl acetate and has 26 wt. % acrylic acid grafted thereto.

8. The film of claim 4, wherein said ethylene/vinyl acetate polymer is an ethylene/vinyl acetate graft copolymer containing 30–36 wt. % vinyl acetate and having 26 wt. % acrylic acid grafted thereto.

9. The film of claim 1, wherein said hydrophilic inclusions consist of a hydrophilic polymer formed from a mixture of acrylic acid/N-vinylpyrrolidone or acrylamide/N-vinylpyrrolidone.

10. The film of claim 1, wherein said inclusions consist of a hydrophilic polymer formed from acrylamide.

11. The film of claim 1, having a thickness of 50–500 microns.

12. The film of claim 1, comprising up to 40 wt. % of said active principle.

13. The film of claim 12, wherein said active principle is selected from the group consisting of non-steroidal anti-inflammatory agents, 17β-oestradiol, progestogen, anticholinesterases, trinitrin, nicotine, morphine, dihydroergotamine, physostigmine, bromocriptine and salicylic acid.

14. The film of claim 13, wherein said active principle is 17β-oestradiol.

15. The film of claim 13, wherein said active principle is a mixture of oestradiol and progestogen.

16. The film of claim 13, wherein said active principle is physostigmine.

17. The film of claim 13, wherein said active principle is trinitrin.

18. The film of claim 13, wherein said active principle is nicotine.

19. The film of claim 13, wherein said active principle is dihydroergotamine.

20. The film of claim 13, wherein said active principle is bromocriptine.

21. The film of claim 13, wherein said active principle is salicylic acid.

22. The film of claim 13, wherein said active principle is a non-steroidal anti-inflammatory agent selected from the group consisting of ketoprofen and ibuprofen.

23. The film of claim 12, further comprising a permeability stimulator selected from the group consisting of alcohols and polyols.

24. A transdermal system, comprising:

an occlusive support, the active principle-containing film of claim 1 in contact with said support, an adhesive interface in contact with said active principle-containing film, and a protective film in contact with said adhesive interface.

25. A transdermal system comprising:

an occlusion support, an active principle-containing film comprising a hydrophobic ethylene/vinyl acetate polymer containing at least one active principle and composed of 10–50 wt. % of hydrophilic inclusions consisting of a hydrophilic polymer formed from at least one hydrophilic monomer selected from the group consisting of acrylamide, ethylene glycol acrylate, methylolacrylamide, diacetone acrylamide, maleic acid, acrylic acid, fumaric acid, itaconic acid, propylene glycol acrylate, ethylene glycol methacrylate, methacrylamide, methacrylic acid, propylene glycol methacrylate, hydroxyethyl methacrylate, dimethylaminoethyl methacrylate, N-vinylpyrrolidone, vinylacetic acid and vinyl sulfonic acids, in contact with said support, an adhesive interface in contact with said active principle-containing film, and a protective film in contact with said adhesive interface.

26. The transdermal system of claim 24 or 25, wherein said occlusive film is selected from the group consisting of polyvinylidene dichlorides, polyethylenes, ethylene/polyvinyl alcohols, polypropylenes, polyesters, polychlorotrifluoroethylenes and combinations thereof with a metal sheet, and said adhesive interface is chemically inert with respect to said active principle-containing film and is selected from the group consisting of acrylic polymers, polyurethanes, silicones and ethylene/vinyl acetate polymers.

27. The transdermal system of claim 24 or 25, wherein said active principle-containing film is an ethylene/vinyl acetate-acrylic acid graft copolymer.

28. The transdermal system of claim 27, wherein said ethylene/vinyl acetate-acrylic acid graft copolymer comprises 18 wt. % vinyl acetate and 26 wt. % acrylic acid.

29. The transdermal system of claim 24 or 25, wherein said active principle-containing film is an ethylene/vinyl acetate-acrylamide graft copolymer.

30. The transdermal system of claim 24 or 25, wherein said active principle-containing film further comprises a permeability stimulator selected from the group consisting of alcohols and polyols.

31. The transdermal system of claim 24 or 25, wherein said active principle-containing film comprises at least two active principles.

32. The transdermal system of claim 24 or 25, wherein said active principle is distributed throughout said active principle-containing film.

33. The transdermal system of claim 31, wherein said active principle-containing film has at least two regions and said at least two active principles are separately distributed in said at least two regions.

34. A process for the preparation of the film of claim 1, comprising the steps of:

(a) contacting a hydrophobic ethylene/vinyl acetate polymer with at least one hydrophilic monomer selected from the group consisting of acrylamide, methylolacrylamide, diacetone acrylamide, maleic acid, acrylic acid, fumaric acid, itaconic acid, propylene glycol acrylate, ethylene glycol methacrylate, methacrylamide, meth-acrylic acid, propylene glycol methacrylate, hydroxyethyl methacrylate, dimethylaminoethyl methacrylate, N-vinylpyrrolidone, vinylacetic acid and vinylsulfonic acids to form a mixture, (b) irradiating said mixture for simultaneously polymerizing said hydrophilic monomers to form hydrophilic polymer and grafting said hydrophilic polymer onto said hydrophobic ethylene/vinyl acetate polymer to form an ethylene/vinyl acetate copolymer having grafted thereto said hydrophilic polymer, to obtain an ethylene/vinyl acetate graft copolymer having a degree of grafting of said hydrophilic polymer of 10–50% to form a copolymer matrix, (c) charging said ethylene/vinyl acetate polymer or said copolymer matrix with an active principle, and (d) shaping said copolymer matrix or said charged copolymer matrix to form a film.

35. The process of claim 34, wherein said irradiating and polymerizing step (b) is carried out in a liquid medium in the presence of an inhibitor of homopolymerization of said hydrophilic monomer.

36. The process of claim 34, wherein said irradiating and polymerizing step (b) is carried out in a liquid medium in the presence of a copolymerizable crosslinking agent.

37. The process of claim 35, wherein said copolymerizable crosslinking agent is selected from the group consisting of methylenebisacrylamide, divinylbenzene, triallyl cyanurate, ethylene, butylene glycol acrylates, butylene glycol methacrylates, tetraethylene glycol acrylates, tetraethylene glycol methacrylates and triallyl orthophosphate.

38. The process of claim 34, wherein said irradiating and polymerizing step (b) is carried out by irradiating with ionizing radiation to provide a total irradiation dose of between 0.5–50 kGy.

39. The process of claim 34, wherein said charging step (c) is carried out before said shaping step (d).

40. The process of claim 34, wherein said charging step (c) is carried out after said shaping step (d).

41. The process of claim 34, wherein said charging step (c) comprises steeping said active principle into said ethylene/vinyl acetate polymer or said copolymer matrix, dispersing said active principle into said ethylene/vinyl acetate polymer or said copolymer matrix, diffusing said active principle into said ethylene/vinyl acetate polymer or said copolymer matrix from a support impregnated with said active principle, or immersing said ethylene/vinyl acetate polymer or said copolymer matrix in a saturated vapor atmosphere of said active principle.

42. The process of claim 34, wherein said shaping step (d) is carried out by extrusion.

43. A process for the preparation of the film of claim 1, comprising the steps of:

(a) irradiating a hydrophobic ethylene/vinyl acetate polymer in the powder, granule, or film form, at a dose between 10–80 kGy, (b) storing the irradiated ethylene/vinyl acetate polymer, (c) contacting said stored irradiated ethylene/vinyl acetate polymer with at least one hydrophilic monomer selected from the group consisting of acrylamide, methylolacrylamide, diacetone acrylamide, maleic acid, acrylic acid, fumaric acid, itaconic acid, propylene glycol acrylate, ethylene glycol methacrylate, methacrylamide, methacrylic acid, propylene glycol methacrylate, hydroxyethyl methacrylate, dimethylaminoethyl methacrylate, N-vinylpyrrolidone, vinylacetic acid, and vinylsulfonic acids to form an ethylene/vinyl acetate copolymer having grafted thereto said hydrophilic monomer in the form of a hydrophilic polymer, to obtain an ethylene/vinyl acetate graft copolymer having a degree of grafting of said hydrophilic polymer of 10–50%, to form a copolymer matrix, (c) charging said ethylene/vinyl acetate polymer or said copolymer matrix with an active principle, and (d) shaping said copolymer matrix or said charged copolymer matrix to form a film.

44. A process for the preparation of an ethylene/vinyl acetate graft copolymer having grafted thereto hydrophilic monomers in the form of a hydrophilic polymer, comprising the steps of:

(a) irradiating a hydrophobic ethylene/vinyl acetate polymer in the powder, granule, or film form, at a dose between 10–80 kGy, (b) storing the irradiated ethylene/vinyl acetate polymer, (c) contacting said stored irradiated ethylene/vinyl acetate polymer with at least one hydrophilic monomer selected from the group consisting of acrylamide, methylolacrylamide, diacetone acrylamide, maleic acid, acrylic acid, fumaric acid, itaconic acid, propylene glycol acrylate, ethylene glycol methacrylate, methacrylamide, methacrylic acid, propylene glycol methacrylate, hydroxyethyl methacrylate, dimethylaminoethyl methacrylate, N-vinylpyrrolidone, vinylacetic acid, and vinylsulfonic acids to form an ethylene/vinyl acetate copolymer having grafted thereto said hydrophilic monomer in the form of a hydrophilic polymer, to obtain an ethylene/vinyl acetate graft copolymer having a degree of grafting of said hydrophilic polymer of 10–50%, to form a copolymer matrix.

* * * * *

UNITED STATES PATENT AND TRADEMARK OFFICE
CERTIFICATE OF CORRECTION

PATENT NO. : 5,556,635
DATED : September 17, 1996
INVENTOR(S) : Michel ISTIN, et al.

It is certified that error appears in the above-indentified patent and that said Letters Patent is hereby corrected as shown below:

On the title page, the information in Item [86] is listed incorrectly and should read:

-- [86] PCT No.: PCT/FR93/01272

§ 371 Date: Oct. 27, 1994

§ 102 (e) Date: Oct. 27, 1994. --

Signed and Sealed this

Seventeenth Day of December, 1996

*Attest:*

BRUCE LEHMAN

*Attesting Officer*　　*Commissioner of Patents and Trademarks*